United States Patent
Faur et al.

(10) Patent No.: US 10,175,197 B2
(45) Date of Patent: Jan. 8, 2019

(54) CROSSTALK COMPENSATION FOR ION MOBILITY SPECTROMETRY POWER SUPPLY

(71) Applicant: DH Technologies Development PTE Ltd., Singapore (SG)

(72) Inventors: Manuel Faur, Richmond Hill (CA);
Tiberiu Gera, Etobicoke (CA);
Bradley B. Schneider, Bradford (CA);
Farshid Tayyeb, Vaughan (CA); John Vandermey, Georgetown (CA)

(73) Assignee: DH Technologies Development Pte. Ltd. (SG)

( * ) Notice: Subject to any disclaimer, the term of this patent is extended or adjusted under 35 U.S.C. 154(b) by 0 days.

(21) Appl. No.: 15/320,561

(22) PCT Filed: Jun. 23, 2015

(86) PCT No.: PCT/IB2015/054711
§ 371 (c)(1),
(2) Date: Dec. 20, 2016

(87) PCT Pub. No.: WO2015/198228
PCT Pub. Date: Dec. 30, 2015

(65) Prior Publication Data
US 2017/0191964 A1 Jul. 6, 2017

Related U.S. Application Data

(60) Provisional application No. 62/015,885, filed on Jun. 23, 2014.

(51) Int. Cl.
*G01N 27/62* (2006.01)
*H01J 49/02* (2006.01)

(52) U.S. Cl.
CPC .......... *G01N 27/624* (2013.01); *H01J 49/022* (2013.01)

(58) Field of Classification Search
None
See application file for complete search history.

(56) References Cited

U.S. PATENT DOCUMENTS

| 5,801,379 A * | 9/1998 | Kouznetsov | .......... H01J 49/022 250/286 |
| 2006/0151693 A1* | 7/2006 | Guevremont | ........ G01N 27/624 250/292 |

(Continued)

FOREIGN PATENT DOCUMENTS

| WO | 2004029604 A2 | 4/2004 | |
| WO | 2012056322 A1 | 5/2012 | |
| WO | WO 2012056322 A1 * | 5/2012 | ........... G01N 27/622 |

OTHER PUBLICATIONS

International Search Report and Written Opinion for PCT/IB2015/054711 dated Oct. 1, 2015.

(Continued)

*Primary Examiner* — Andrew Smyth

(57) ABSTRACT

Apparatus, systems, and methods for reducing or eliminating crosstalk in ion mobility spectrometers are provided. In some aspects, the apparatus, systems, and methods can reduce or eliminate crosstalk without significantly increasing the overall capacitive load of the ion mobility system. In accordance with various aspects of the applicant's teachings, cross talk compensation circuits are disclosed herein that address resulting issues in RF pickup and/or crosstalk in ion mobility spectrometers used with high-sensitivity downstream mass spectrometers such as mass spectrometers having high velocity gas interfaces that can be coupled to the ion mobility spectrometer.

7 Claims, 19 Drawing Sheets

(56) References Cited

U.S. PATENT DOCUMENTS

| | | | |
|---|---|---|---|
| 2009/0140138 A1* | 6/2009 | Vandermey | G01N 27/624 250/282 |
| 2009/0189064 A1 | 7/2009 | Miller et al. | |
| 2009/0212207 A1* | 8/2009 | Griffin | G01N 27/624 250/282 |
| 2011/0049353 A1* | 3/2011 | Gilbert | G06K 9/0051 250/282 |
| 2011/0248157 A1* | 10/2011 | Sugiyama | H01J 49/063 250/282 |

OTHER PUBLICATIONS

Purves R W et al. "Mass Spectrometric Characterization of a High-Field Asymmetric Waveform Ion Mobility Spectrometer", Review of Scientific Instruments, 69:12, pp. 4094-4105, Dec. 1998.

* cited by examiner

CROSSTALK COMPENSATION FOR ION MOBILITY SPECTROMETRY POWER SUPPLY

RELATED APPLICATION

This application claims priority to U.S. provisional application No. 62/015,885, filed on Jun. 23, 2014, which is incorporated herein by reference in its entirety.

BACKGROUND

Differential mobility spectrometry separates ions based upon the difference between high and low field mobility, typically at or near atmospheric pressure. Ions drift through a mobility cell, typically having two electrodes separated by a substantially uniform gap, and are separated by exposure to alternating high and low electric field conditions. The separation field is controlled by application of an asymmetric waveform to electrodes within the mobility cell. Depending on the difference between the high-field and low-field mobility of an ion, it will migrate toward one or the other electrode. A small DC field can be applied between the electrodes to steer ions back to the central axis of the mobility cell such that they may be transmitted to a downstream detector, or instrument such as a mass spectrometer. Only ions with specific differential mobility will pass through the device.

The dominant analyzer geometries that are used today are characterized by either flat planar electrodes providing a homogeneous electric field, or curved cell geometries that create inhomogeneous fields. The former is popularly referred to as a differential mobility spectrometer (DMS), and the latter is referred to as High Field Asymmetric Waveform Ion Mobility Spectrometry (FAIMS) (collectively referred to herein as ion mobility spectrometers). The present teachings will be described in conjunction with specific DMS configurations, but are also applicable to FAIMS devices. Together, these devices can be called ion mobility spectrometry devices.

Ion separation can be manifested under the influence of a strong asymmetric waveform, typically referred to as separation voltage (SV). The SV is most commonly generated using sin wave outputs. One way of accomplishing an appropriate SV field within an ion mobility cell in a DMS is described in U.S. Pat. No. 7,838,822, which is concurrently owned and hereby incorporated by reference in its entirety. This exemplary method creates the SV by applying two discrete sin waves to the mobility cell, for example a 3 MHz sin wave on the first electrode, and a 6 MHz sin wave with half the amplitude on the second electrode. The net effect with this approach is a waveform, which will be referred to herein as a FAIMS waveform, as shown in FIG. 1, and which can be utilized in either a DMS or FAIMS, A proper FAIMS waveform has the characteristic that results in an electric field in the mobility cell that is asymmetric and has a time-averaged value substantially equal to zero.

SV6 is a low amplitude, high frequency signal; SV3 is a high amplitude (approximately twice the voltage), low frequency (half the frequency) signal. (The 3 MHz sin wave is shown in green and the 6 MHz sin wave is shown in orange.) The net effect is the separation waveform shown in the burgundy trace. It should be appreciated that SV6 and SV3 are harmonics, which allows for a stable FAIMS waveform. The existing approaches to generating FAIMS waveforms have utilized DMS mobility cells having substantially less capacitance than the other capacitances in the DMS system.

SUMMARY

Apparatus, systems, and methods in accordance with the applicant's present teachings allow for the reduction in or elimination of electrical crosstalk in ion mobility spectrometers, and in sonic aspects, without significantly increasing the overall capacitive load of the ion mobility system (spectrometer). In accordance with various aspects of the applicant's teachings, several exemplary embodiments of cross talk compensation circuits are disclosed that address resulting issues in RF pickup and/or crosstalk when the ion mobility spectrometer is configured for use (e.g., elongated relative to known ion mobility spectrometers) with high-sensitivity downstream mass spectrometers, such as mass spectrometers having high velocity gas interfaces that can be coupled to the ion mobility spectrometer.

In accordance with various aspects of the applicant's teachings, an ion mobility system is provided that comprises an ion mobility cell comprising at least a first and a second electrode that are substantially uniformly spaced, the ion mobility cell having a cell capacitance; a first high-voltage waveform generator configured to produce a first temporally periodic signal (e.g., sinusoidal signal) at a first frequency and at a first amplitude, the first waveform generator electrically coupled to the first electrode; a second high-voltage waveform generator configured to produce a second temporally periodic signal (e.g., sinusoidal signal) at a second frequency and at a second amplitude, the second waveform generator electrically coupled to the second electrode, the second frequency being a harmonic of the first frequency; and, a crosstalk compensation circuit configured to reduce crosstalk between the first and second electrodes such that application of the first and second temporally periodic signals results in an electric field in the ion mobility cell that is asymmetric and has a time-averaged value substantially equal to zero.

Crosstalk compensation circuits in accordance with the present teachings can have a variety of configurations. For example, in sonic aspects, the crosstalk compensation circuit can comprise a first filter electrically coupled to the first electrode and configured to substantially filter signal components at the second frequency and a second filter electrically coupled to the second electrode and configured to substantially filter signal components at the first frequency. For example, the first and second filters can be notch filters. In some aspects, the crosstalk compensation circuit comprises a third order circuit in parallel to the cell capacitance. By way of example, the third order circuit can comprise a first and a second inductor placed in series and a capacitor placed in parallel to the second inductor. In related aspects, the second inductor can have an inductance value about half of the inductance value of the first inductor.

In some aspects, the crosstalk compensation circuit can comprise a transformer that magnetically couples the first and second electrodes. For example, the transformer can comprise a first winding corresponding to the first electrode and a second winding corresponding to the second electrode, wherein the first winding is electrically coupled to the first electrode and the second winding is in electrical communication with the second winding via capacitor. In some aspects, the capacitor can have a capacitance substantially equal to the cell capacitance.

In some aspects, a mass spectrometer can be coupled to an output of the ion mobility cell. In some aspects, the ion mobility cell can be one of a DMS and a FAIMS.

In accordance with various aspects of the applicant's teachings, a high-field asymmetric-waveform apparatus is provided that comprises a first high-voltage waveform generator configured to produce a first temporally periodic signal (e.g., sinusoidal signal) at a first frequency and at a first amplitude, the first waveform generator configured to electrically couple to a first electrode of an ion mobility cell; a second high-voltage waveform generator configured to produce a second temporally periodic signal (e.g., sinusoidal signal) at a second frequency and at a second amplitude, the second waveform generator configured to electrically couple to a second electrode of the ion mobility cell, the second frequency being a harmonic of the first frequency; and a crosstalk compensation circuit configured to reduce crosstalk between the first and second electrodes such that electrical signals at the first and second electrodes are configured to create an electric field in the ion mobility cell that is asymmetric and has a time-averaged value substantially equal to zero.

In accordance with various aspects of the applicant's teachings, a method for reducing crosstalk in an ion mobility spectrometer is provided. The method comprises providing a first temporally periodic signal (e.g., sinusoidal signal) at a first frequency and at a first amplitude with a first waveform generator, the first waveform generator electrically coupled to a first electrode of an ion mobility cell; providing a second temporally periodic signal (e.g., sinusoidal signal) at a second frequency and at a second amplitude with a second waveform generator, the second waveform generator electrically coupled to a second electrode of the ion mobility cell, the second frequency being a harmonic of the first frequency; and utilizing a crosstalk compensation circuit to reduce crosstalk between the first and second electrodes such that application of the first and second temporally periodic signals results in an electric field in the ion mobility cell that is asymmetric and has a time-averaged value substantially equal to zero.

In some aspects, the crosstalk compensation circuit can comprise a first filter electrically coupled to the first electrode and configured to substantially filter signal components at the second frequency and a second filter electrically coupled to the second electrode and configured to substantially filter signal components at the first frequency. The first and second filters can be notch filters.

In some aspects, the first and second electrodes of the ion mobility cell can be substantially uniformly spaced, and the ion mobility cell exhibits a cell capacitance. In related aspects, the crosstalk compensation circuit can comprise a third order circuit in parallel to the cell capacitance. By way of example, the third order circuit can comprise a first and a second inductor placed in series and a capacitor placed in parallel to the second inductor. In some aspects, the second inductor can have an inductance value that is about half of an inductance value of the first inductor.

In some aspects, the crosstalk compensation circuit can comprise a transformer that magnetically couples the first and second electrodes. For example, the transformer can comprise a first winding corresponding to the first electrode and a second winding corresponding to the second electrode, wherein the first winding is electrically coupled to the first electrode and the second winding is in electrical communication with the second winding via capacitor. In related aspects, the capacitor can have a capacitance substantially equal to the capacitance of the ion mobility cell.

In some aspects, the method can comprise providing a mass spectrometer coupled to an output of the ion mobility cell. In some aspects, the ion mobility cell can have a length greater than about 3 cm (e.g., about 13 cm).

These and other features of the applicant's teachings are set forth herein.

DETAILED DESCRIPTION OF EXEMPLARY EMBODIMENTS

There is a commercial desire to move towards more sensitive DMS/mass spectrometer interfaces. One approach to achieve efficient transfer of ions from the DMS cell to a mass spectrometer involves sealing the mobility cell to a vacuum inlet of the mass spectrometer, such that the gas flow into the vacuum draws laminar flow streamlines through the mobility cell. In this manner, the gas flow through the mobility cell converges on the mass spectrometer inlet as has been described in U.S. Pat. No. 8,084,736, which is concurrently owned and hereby incorporated by reference in its entirety. The gas flow rate through the DMS cell can thus be dictated by the throughput of the mass spectrometer inlet, although adjustments may be made by adding or removing gas prior to the inlet.

Figure 2:
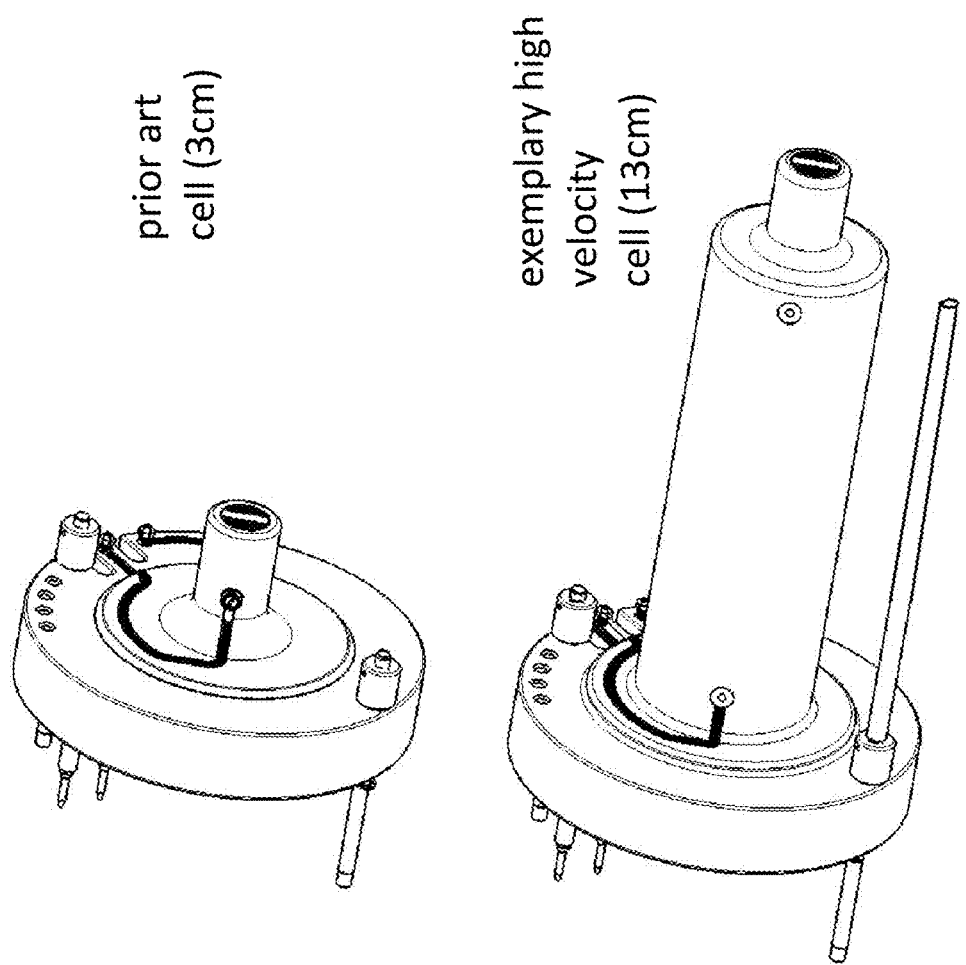
FIG. 2 shows a prior art and exemplary configuration of a mobility cell using the within teachings.

Mass spectrometer sensitivity can be improved by increasing the area of the inlet orifice in order to transfer more ions into the instrument vacuum system. However, this will also increase the flow rate of gas through a DMS device sealed to the vacuum inlet. Therefore, to prevent a general degradation of DMS performance, it is necessary to increase the residence time within the mobility cell to compensate for the increased gas flow. This increased velocity requires an increased functional volume within the electrodes (i.e. longer or wider electrodes) to allow ions sufficient time in the electric fields within the mobility cell to manifest separation based on their field mobility. An exemplary new configuration (1.5 mm orifice diameter with approximately 16 L/min gas throughput) requires elongation of the mobility cell from 3 cm to approximately 13 cm, as shown in FIG. 2. Using these longer mobility cells, ions at the higher velocity can be exposed to substantially similar residence times as prior art mobility cells (such as SelexION™ Technology from AB SCIEX), allowing a similar resolution for the differential mobility of the ions.

Applicant, however, has discovered that using a commercial DMS waveform generator (SelexION™ Technology from AB SCIEX) to evaluate the performance of the elongated DMS cell unexpectedly results in distortions to the FAIMS waveform. The mobility cell has a predetermined capacitance due to the geometry of the parallel electrodes, material of the holder, and gap height. The capacitive load of the exemplary prior art cells is around 15 pF, while the capacitive load for the remaining DMS system measured at the mobility cell is approximately 50 pF. As such, the system capacitance is substantially more than the capacitance of the ion mobility cell in prior art ion mobility cells. In contrast, the capacitive load measured on an exemplary high velocity ion mobility cell is approximately 38 pF. Therefore, the new, elongated mobility cell has a much higher capacitance relative to the total system capacitance than prior art cells. Furthermore, there is a desire to lower the overall system capacitance beyond 50 pF to make the system more efficient, potentially increasing the ratio of cell to system capacitance further.

Figure 3:
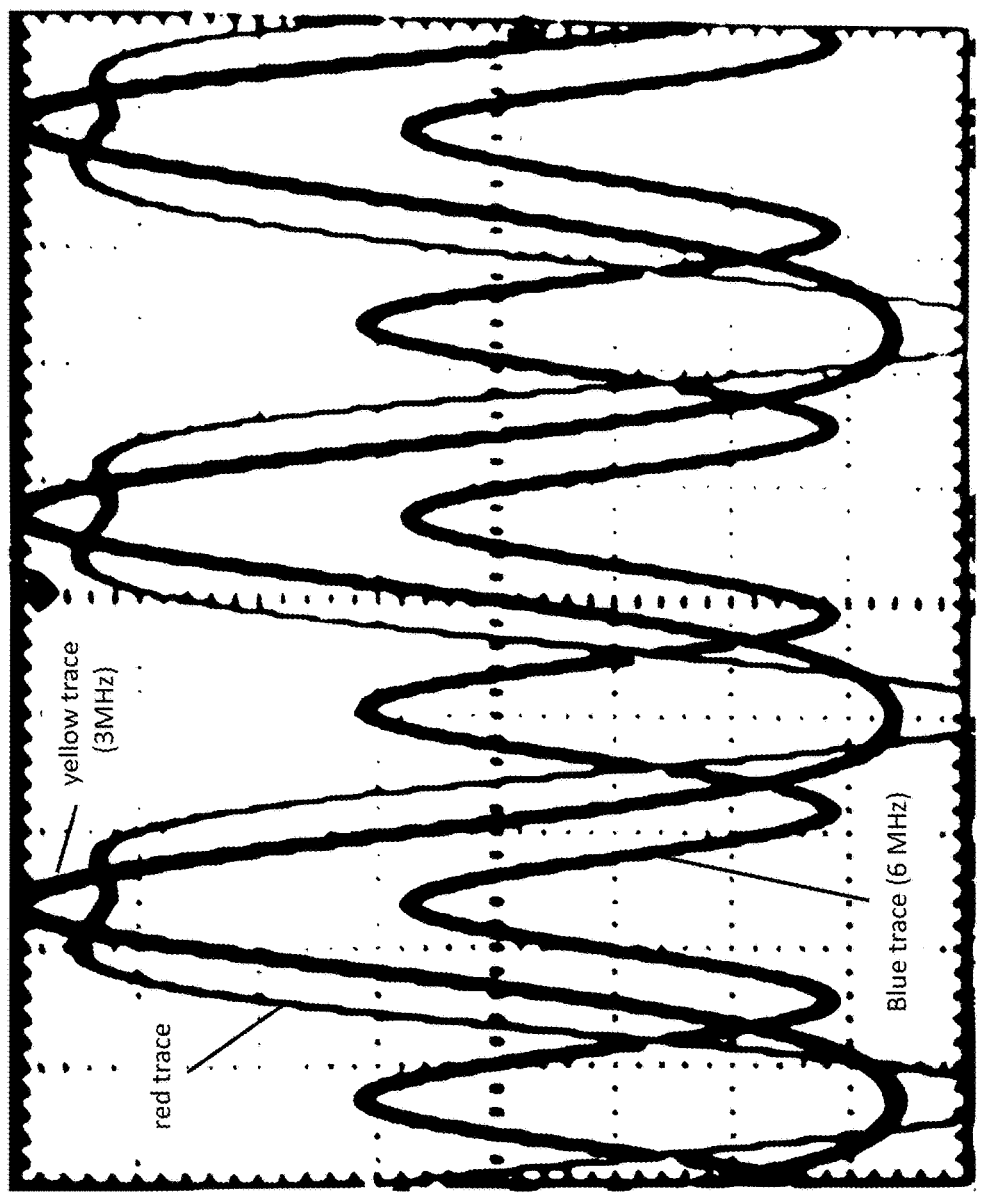
FIG. 3 shows the effect of RF pick-up across the electrode gap on the resulting waveform.

Given that impedance scales inversely with capacitance, the impedance across the electrode gap can become too small when using the elongated cell with a standard shielded wiring harness. The net result is substantial RF pick-up across the gap from one electrode to the other. An example of a measurement of this phenomenon is shown in FIG. 3.

Figure 1:
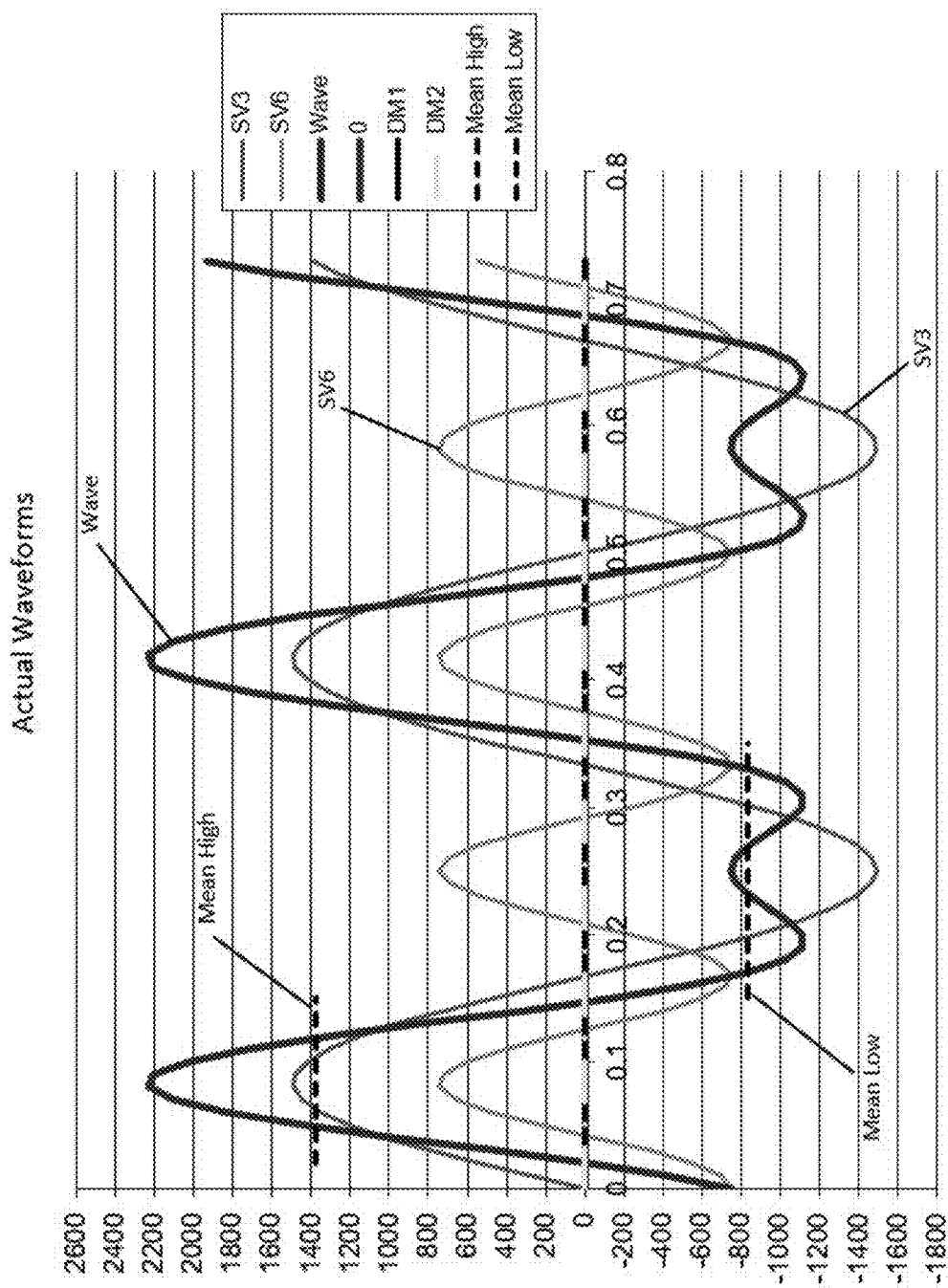
FIG. 1 shows a desired DMS or FAIMS waveform.

RF pick-up across the gap is evident in the 6 MHz waveform (blue trace, lower amplitude), 3 MHz waveform (yellow trace, higher amplitude), and combined waveform (red trace) Referring first to the blue trace, the addition of a component of the 3 MHz waveform skews the 6 MHz trace such that there is a difference in amplitude for each successive maximum in the waveform. The effect of pick-up on the 3 MHz trace (yellow) manifests itself in a skewing of the waveform, with a broadening of the waveform minima relative to the maxima. Finally, the net waveform in the mobility cell is shown in the red trace, where the overall waveform shape is very different than the expected shape from FIG. 1. The waveform shown in FIG. 3 does not provide an optimal separation of ions in DMS. A partial compensation can be achieved by increasing the amplitude of the 6 MHz harmonic relative to the 3 MHz harmonic. However, the net effect is still a different waveform relative to the desired shape of FIG. 1.

Figure 4:
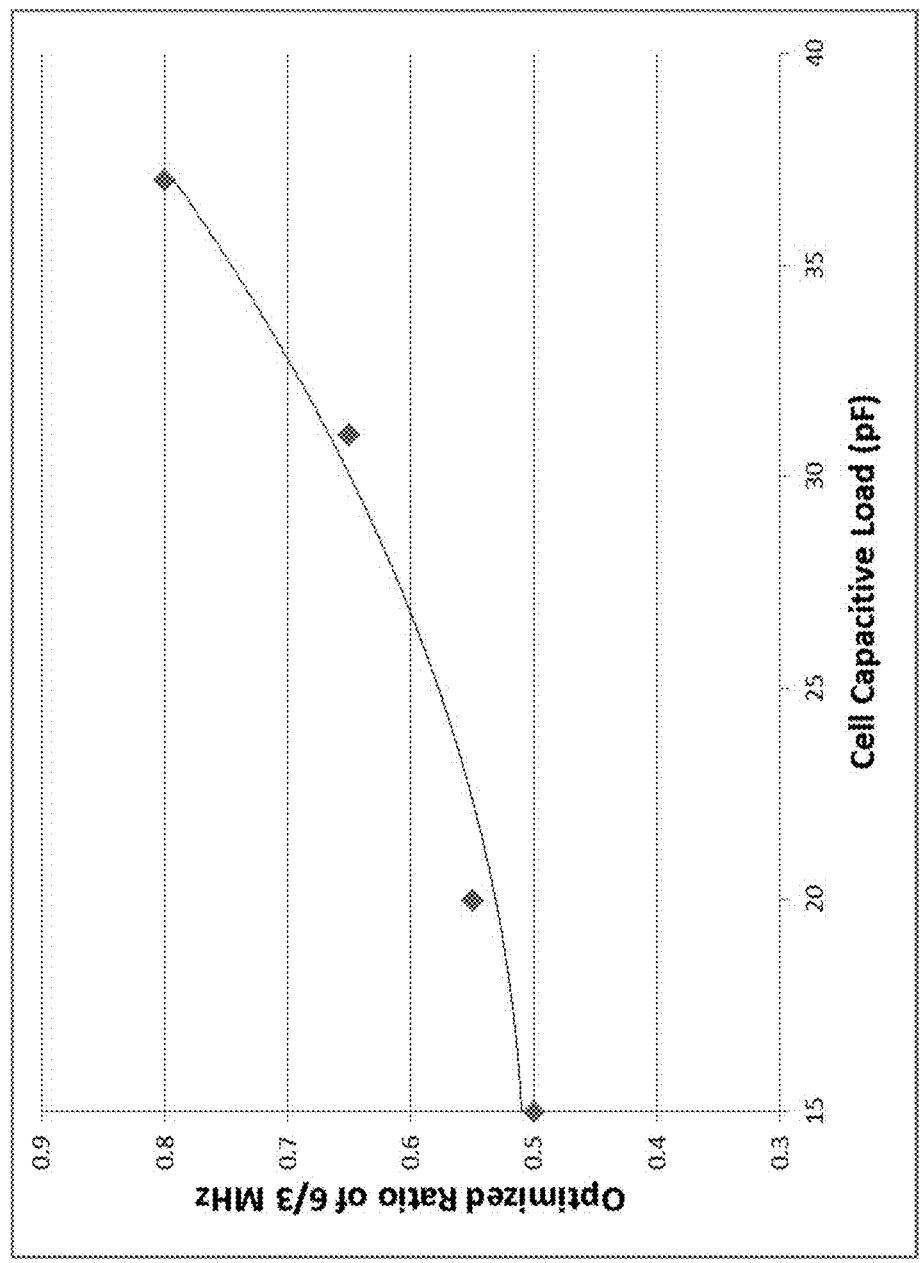
FIG. 4 shows the effect of increasing cell capacitive load on the optimum ration of 6/3 Mhz sin waves.

The magnitude of the waveform distortion can be approximated by experimenting with the optimum ratio of 6/3 MHz waveforms. The ratio of amplitudes for an ideal 2-sin wave generator should correspond to 0.50, while the frequencies differ by a factor of two. However, as the RF pick-up increases, which creates crosstalk between the signals at the electrodes, the magnitude of the 6 MHz waveform needs to increase significantly to maximize the observed compensation voltage (CoV) shifts. CoV is the DC voltage applied between the two DMS electrodes to steer ions to the center of the analytical gap, thus allowing them to be transmitted to the downstream mass spectrometer. In the case of ions that exhibit Type C mobility behavior (mobility decreases with increasing field), the waveform shape can be optimized by maximizing the CoV shift for a given compound. An example of this is presented in FIG. 4, where it is apparent that even small increases in cell capacitive load over the exemplary prior art value (15 pF) can be accompanied by substantial RF pick-up. Accordingly, an increase in the cell capacitance, without additional crosstalk compensation will require re-optimization and/or redesign of the waveform generator. This is particularly problematic because the optimized ratio of the two harmonic outputs becomes a complex function of system capacitance and cell capacitance. Additionally, even after adjusting the ratio of 6/3 MHz harmonics for the data with an approximately 38 pF cell (FIG. 4), it was not possible to completely duplicate the desired waveform of FIG. 1. Therefore, the achievable peak capacity for DMS separations was limited from the ideal case.

Figure 5:
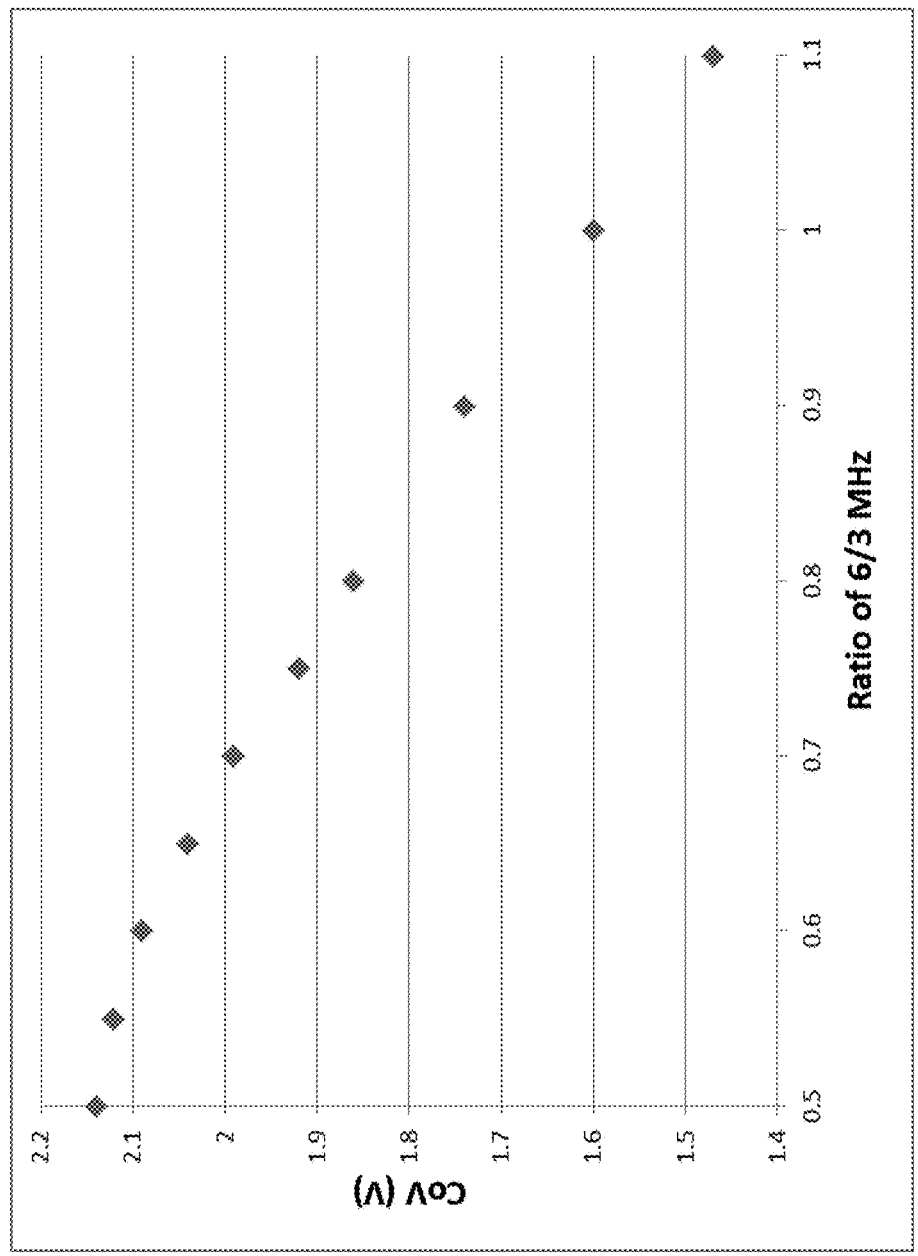
FIG. 5 shows the CoV shift for reserpine ions when RF pickup is eliminated.

A low CoV can indicate that the FAIMS waveform fails to create an asymmetric field with optimized shape, such that less compensation is needed. For an ion exhibiting Type C mobility behavior, the theoretical ideal CoV should be achieved when the low frequency harmonic has approximately twice the amplitude of the high frequency harmonic. FIG. 5 shows the exemplary effect on CoV when RF pickup is eliminated from the system.

Without being bound by any particular theory, the magnitude of the RF pick-up issue is believed to be proportional to the ratio of the capacitive load of the mobility cell to the total DMS system capacitive load when using the exemplary FAIMS waveform approach described above with reference to U.S. Pat. No. 7,838,822, which is incorporated by reference in its entirety. The crosstalk from the RF pickup can be problematic because, without some compensation, it may limit mobility cell designs to small cells that may not be compatible with high-sensitivity mass spectrometer instruments (e.g., having high velocity gas interfaces), and/or it may force an increase in the system capacitive load, such that the load of the mobility cell is maintained small relative to total system capacitance. Moreover, because power requirements scale with capacitive load, it may be desirable to reduce overall system capacitance, which further affects the ratio of the capacitive load of the mobility cell to the total DMS system capacitive load. In accordance with various aspects of the applicant's teachings, several exemplary embodiments of cross talk compensation circuits are disclosed herein to address resulting issues in RF pickup and/or crosstalk.

Figure 6:
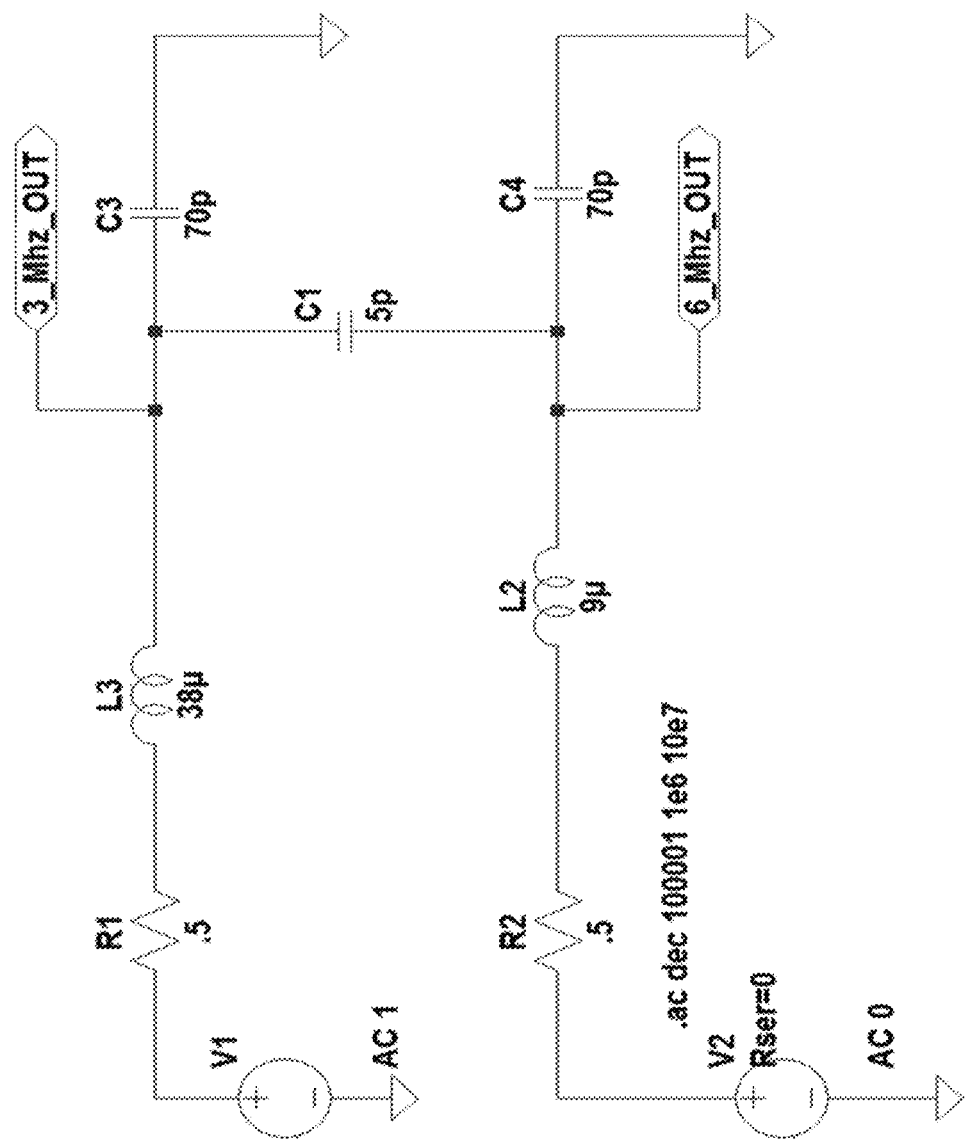
FIG. 6 shows a prior art circuit model for a DMS drive circuit in a mobility cell.

FIG. 6 shows a prior art circuit model for a DMS drive circuit and mobility cell. V1 and V2 are AC drive signals that supply FAIMS waveforms to mobility cell C1, These voltage sources come from high voltage waveform generators that are configured to produce temporally periodic signals (e.g., sinusoidal signals) at a first and second frequency at two different amplitudes to form the FAIMS waveform. in one embodiment, V1 supplies a 3 MHz waveform. R1 and L3 are included to allow resonance at 3 MHz in light of system and mobility cell capacitance. C3 and C4 are the parasitic capacitance for the signal cables and the rest of the DMS system. C1 is the parasitic capacitance for a mobility cell. C1 in FIG. 6 corresponds to an exemplary 13 cm elongated mobility cell. It should be appreciated that future design choices may be made to reduce the capacitance of C3 and C4 to improve efficiency and performance. This circuit will be susceptible to crosstalk across cell C1 as explained above.

Figure 7:
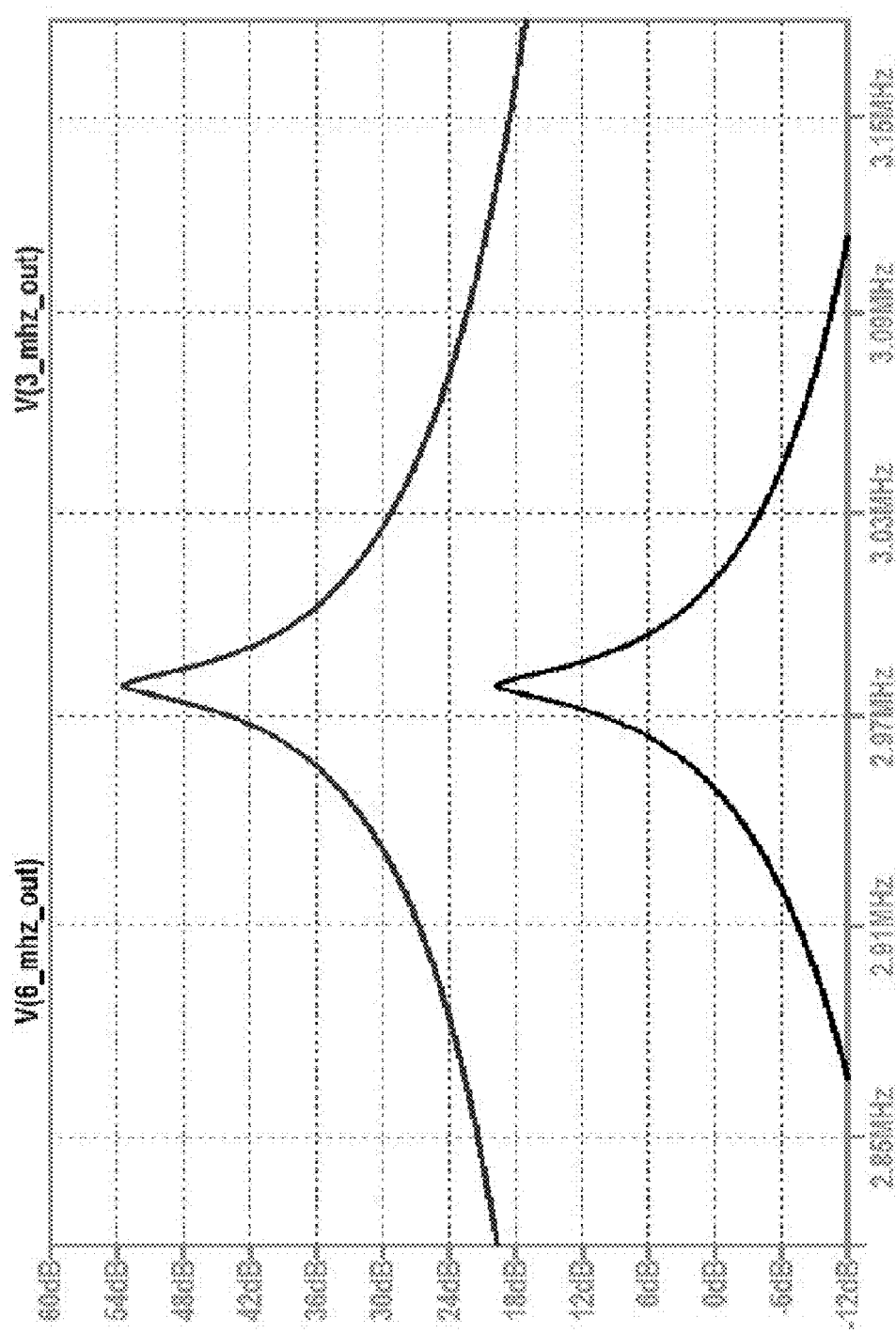
FIG. 7 shows a typical signal during operation of the DMS circuit of FIG. 6 that shows the crosstalk at 3 Mhz.

FIG. 7 shows a typical signal during operation of the DMS drive circuit of FIG. 6, as measured at each side of C1. FIG. 7 shows the crosstalk at 3 MHz. The uppermost signal is the intended 3 MHz signal. The bottom signal is the 3 MHz signal measured on the other side of cell C1, caused by crosstalk. The magnitude of the lower signal is undesirable.

Figure 8:
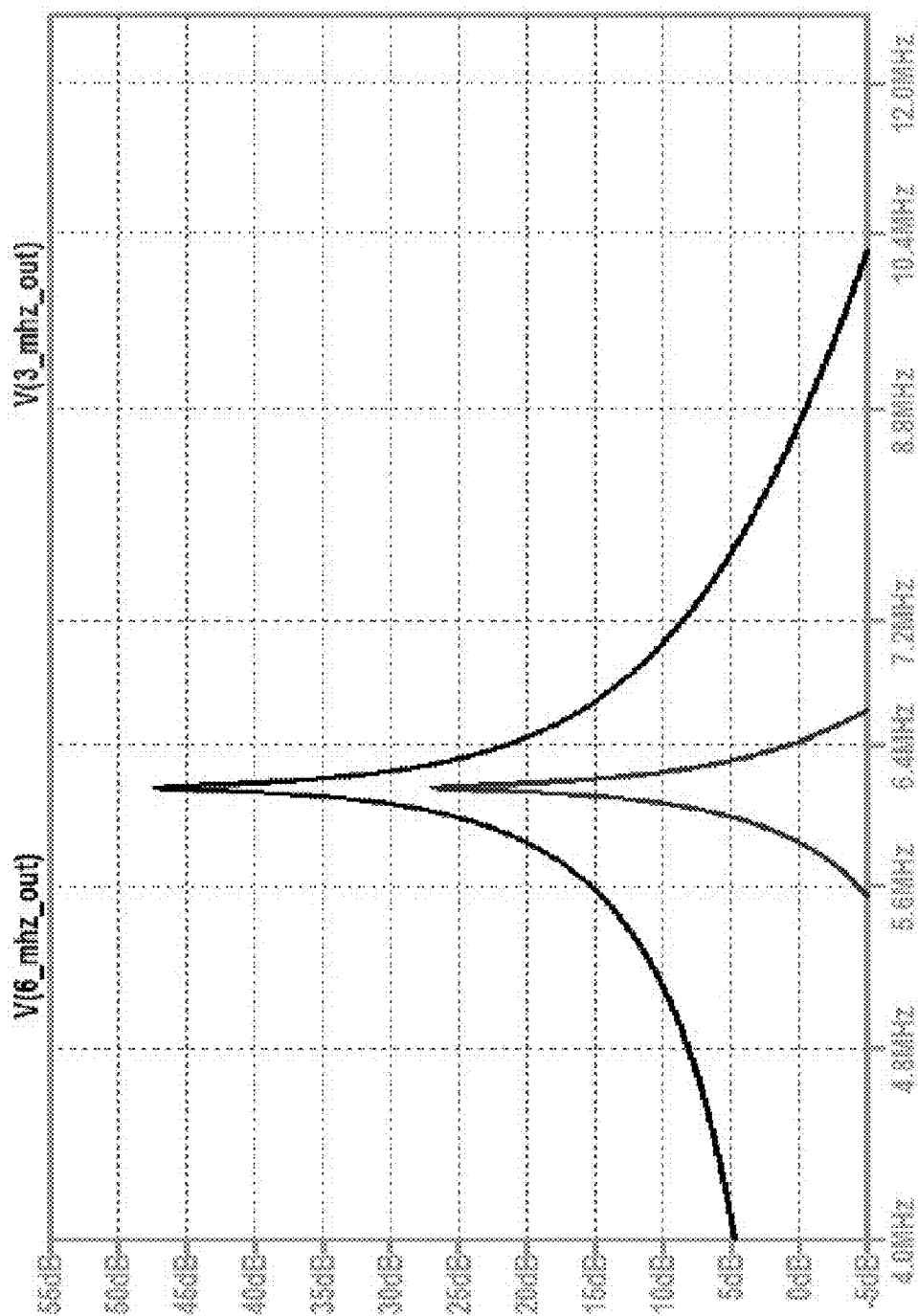
FIG. 8 shows a typical signal during operation of the DMS circuit of FIG. 6 that shows the crosstalk at 6 Mhz.

FIG. 8 is a typical signal during operation of the DMS drive circuit of FIG. 6, as measured at each side of C1 at 6 MHz. Here, the bottom signal represents the crosstalk component measured on the 3 MHz side of C1. Again, the magnitude of the lower signals illustrates an undesirable level of crosstalk.

Figure 9:
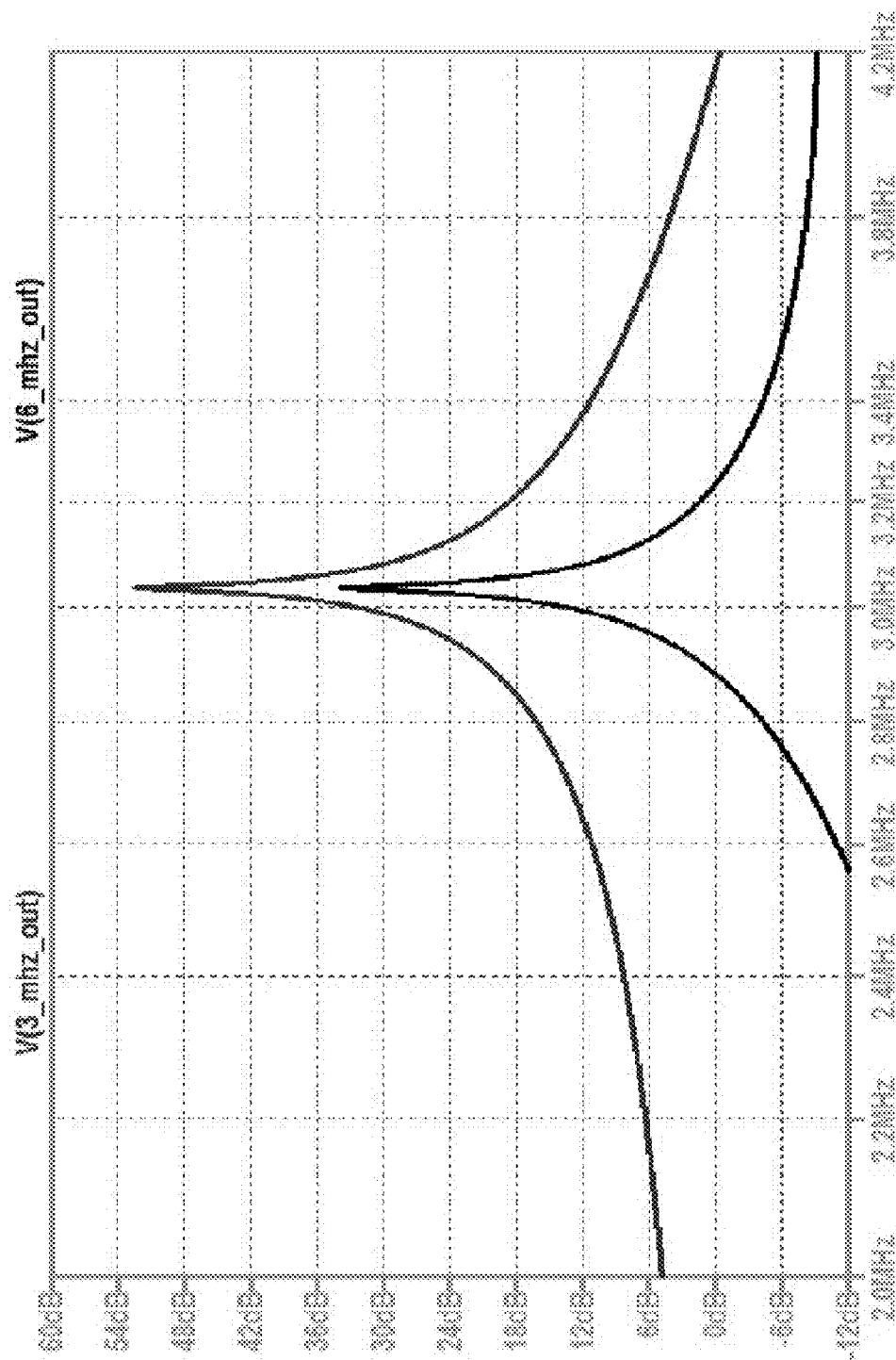
FIG. 9 shows the crosstalk components at 3 Mhz over a wider range of frequencies.

FIG. 9 shows the crosstalk components at 3 MHz over a wider range of frequencies. These signals were measured when the system capacitance C3 and C4 were reduced, illustrating that the crosstalk component (bottom signal) is undesirable when system capacitance is low relative to cell capacitance. That is, the crosstalk component (bottom signal) shows a greatly increased amount of crosstalk as the ratio of cell capacitance/system capacitance increases.

Figure 10:
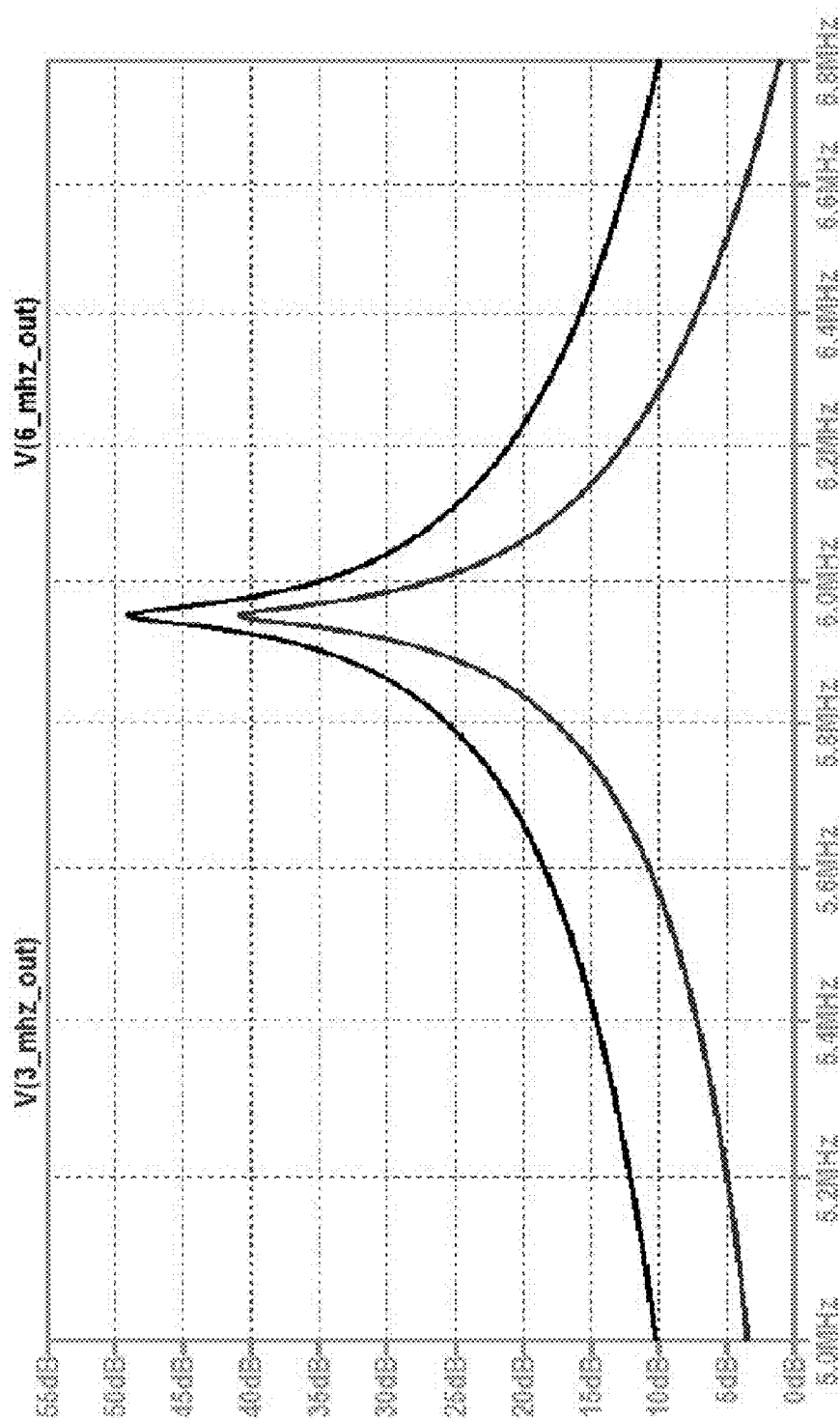
FIG. 10 shows the effect of lowering system capacitance at 6 Mhz.

FIG. 10 shows the same effect of lowering system capacitance at 6 MHz. Note that the crosstalk component (bottom signal) shows a greatly increased amount of crosstalk, within 10 dB of the signal. As shown, the crosstalk component at 6 MHz can be quite problematic when system capacitance is reduced. Accordingly, there is a need for systems and methods to compensate for the inherent crosstalk across mobility cell C1.

Compensation Circuit 1

Figure 11:
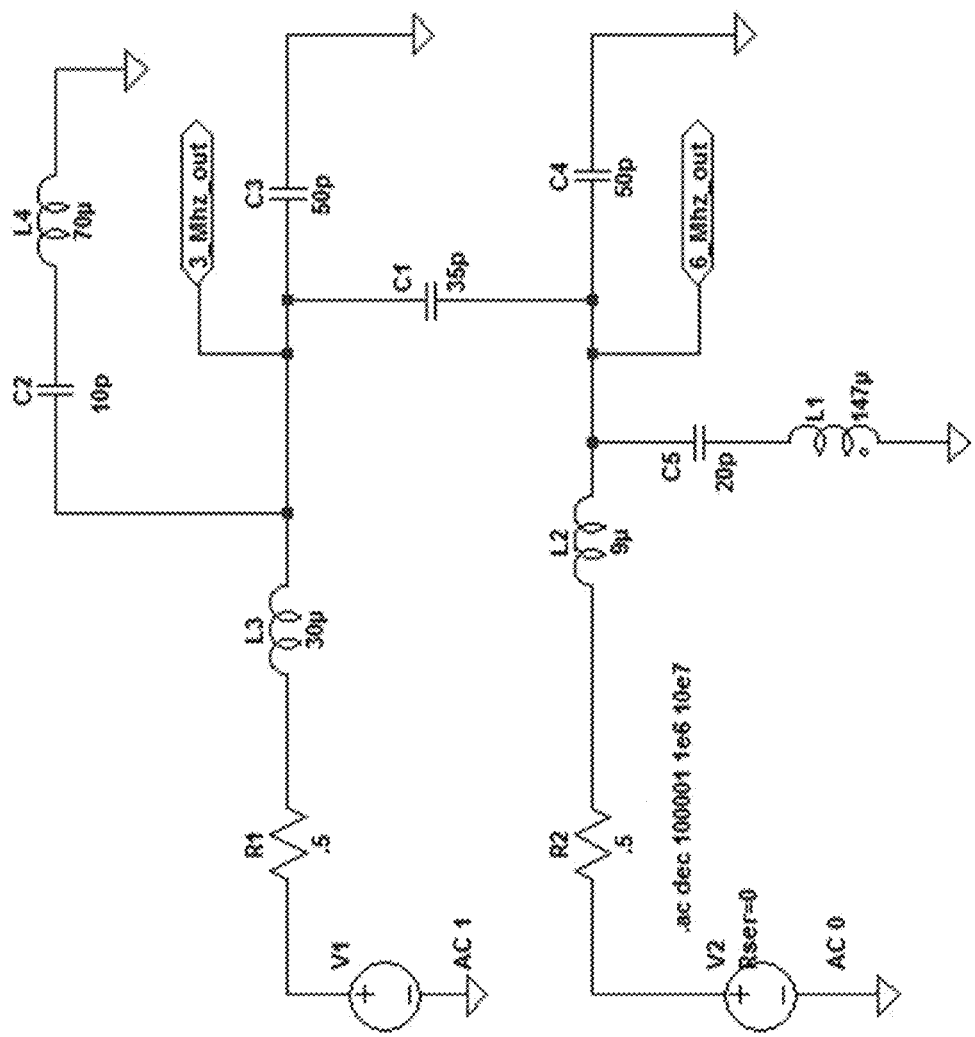
FIG. 11 shows an exemplary embodiment of a crosstalk compensation circuit that uses notch or trap filters.
Figure 12:
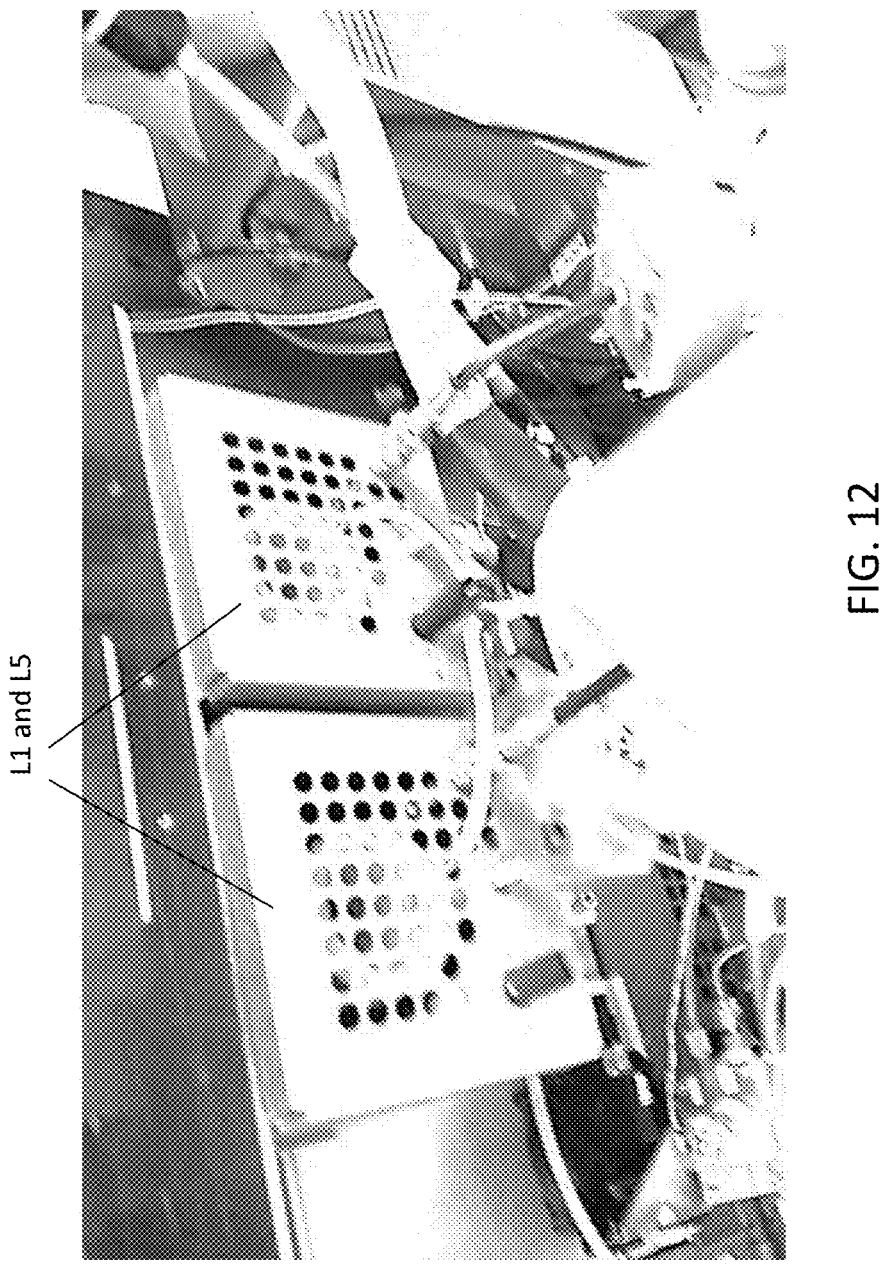
FIG. 12 shows a digital photograph of notch filter coils.

With reference now to FIG. 11, one exemplary embodiment of a circuit diagram for a crosstalk compensation circuit in accordance with various aspects of the applicant's teachings is depicted. The exemplary crosstalk compensation circuit depicted in FIG. 11 addresses the increased capacitance of the mobility cell relative to system capacitance by utilizing notch filters to reduce or eliminate the pick-up issue. In this approach, a 6 MHz filter is electrically coupled to the 3 MHz circuit in the region where shielded wires attach to the mobility cell posts. The 6 MHz filter includes a coil L4 connected via a capacitor C2 to ground, to filter any 6 MHz signal from the 3 MHz side. Similarly, a 3 MHz filter is electrically coupled to the 6 MHz circuit in the region where the shielded wires attach to the cell posts. 3 MHz filter includes a coil L1 connected to ground via a capacitor C5 to filter any 3 MHz signal from the 6 MHz side. These filters can be described as notch filters or trap filters. FIG. 12 shows a digital photograph of the notch filter coils L1 and L5.

Figure 13:
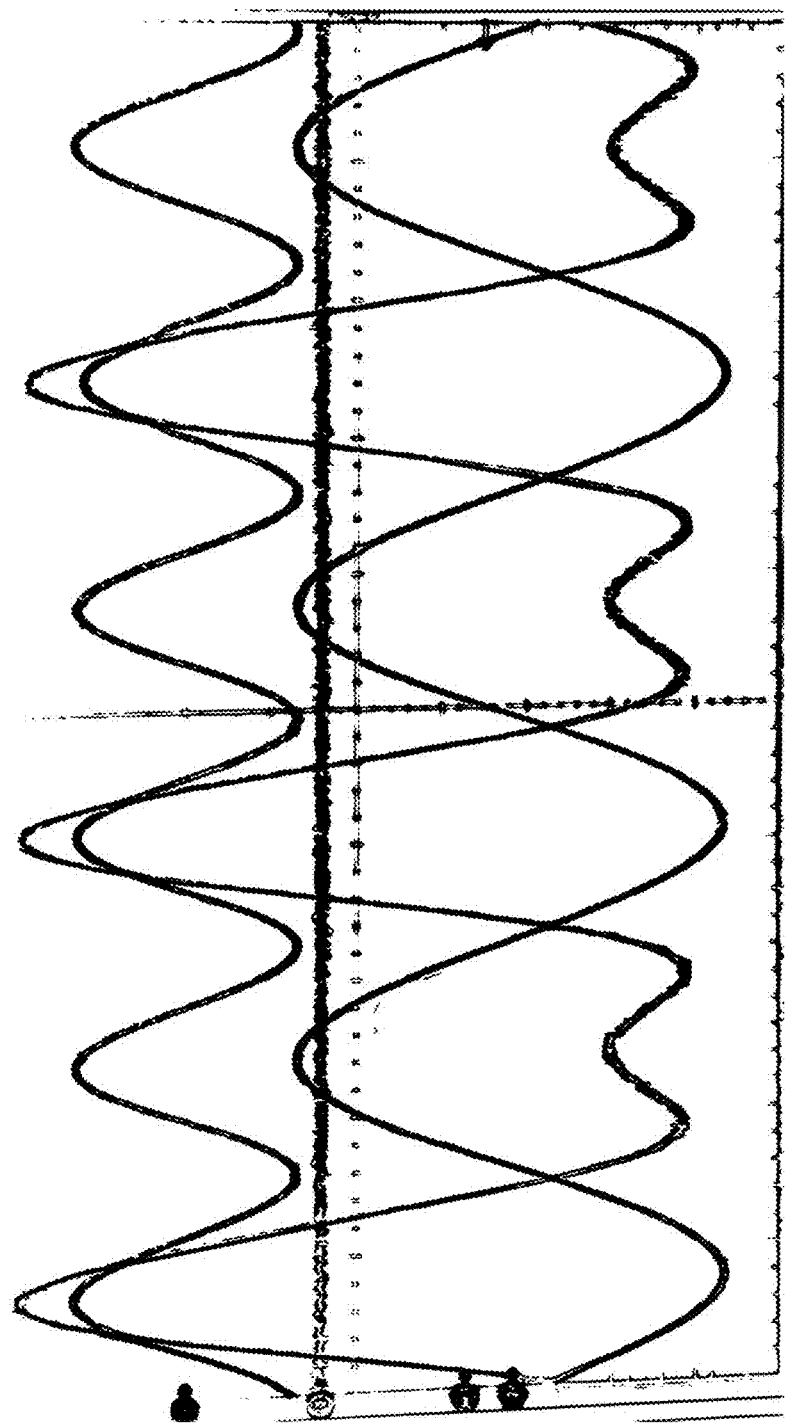
FIG. 13 shows an example of a generated waveform utilizing notch filters.

This solution has been tested in the lab and shown to be effective. Experiments were conducted to verify that the notch filter approach could greatly reduce or substantially eliminate the issue with RF pick-up across the DMS gap. FIG. 13 shows the dramatic improvement that was observed after implementing the notch filters on the system. Distortions of the 3 and 6 MHz waveforms are no longer apparent, and the net effect in the DMS gap is a properly shaped FAIMS waveform. Notice the similarity between the waveforms in FIG. 13 and FIG. 1. The correction of the waveform was further verified by measuring the ratio of the 2 harmonics necessary to achieve the greatest CoV shifts. In the case of undistorted waveforms, the optimum ratio of the 6 MHz waveform to the 3 MHz waveform should be around 0.5. This ratio was confirmed by adjustment of the ratio (fixed p-p amplitude) while monitoring the CoV shift for reserpine ions as shown in FIG. 5. Once the notch filters were in place, the optimum ratio matched the theoretical optimum amplitude ratio for a two sin wave FAIMS generator.

Figure 14:
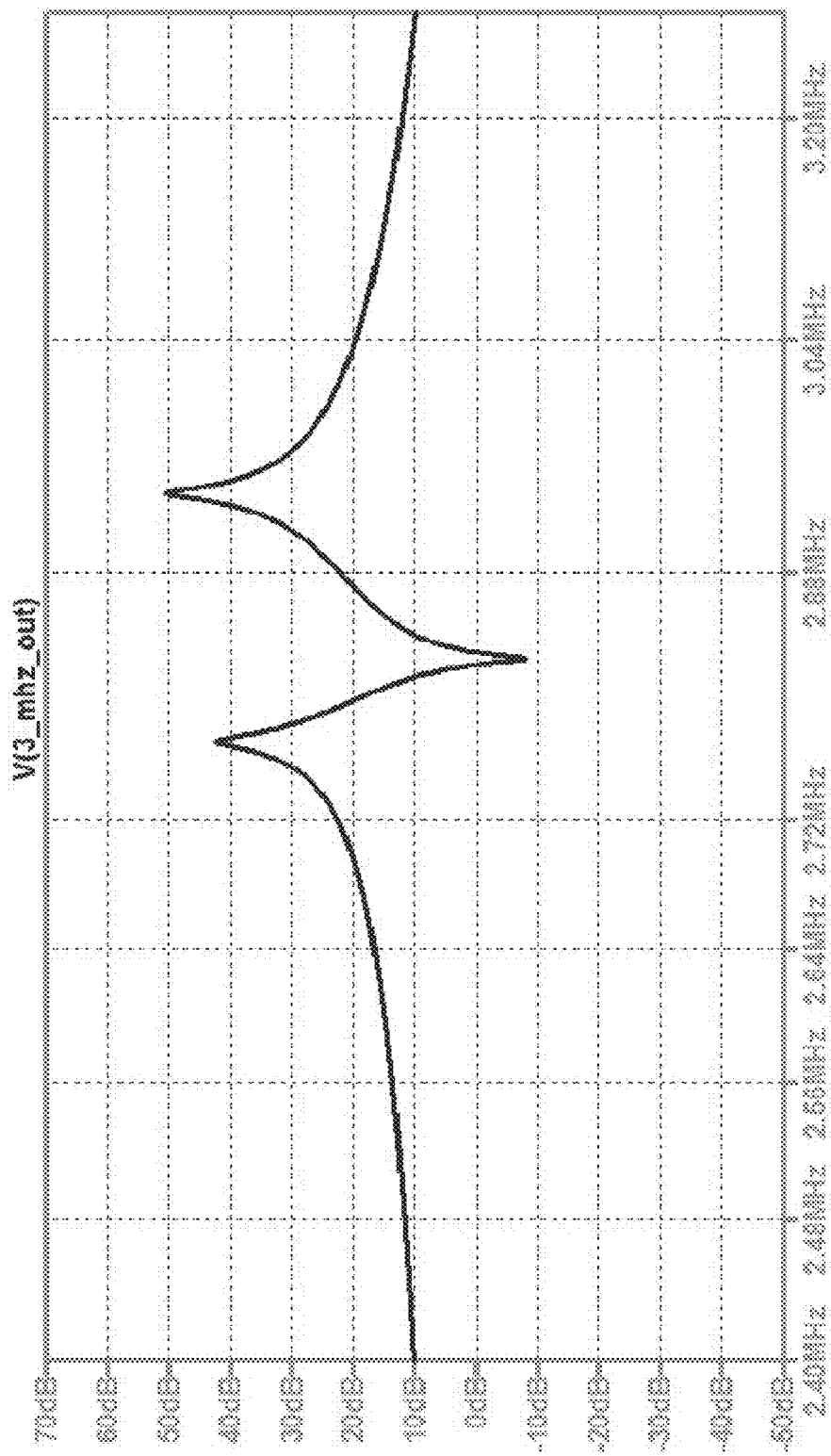
FIG. 14 shows the effect of the use of notch filters on the 3 MHz signal.

FIG. 14 shows the effect of the notch filters on the 3 MHz signal. Here, the gain of the 3 MHz signal on the 3 MHz side of the mobility cell is shown. By picking one of the two peaks, or by tuning the filter so that one of the two peaks corresponds with the FAIMS drive signal, reasonable gain can still be achieved while reducing crosstalk.

Figure 15:
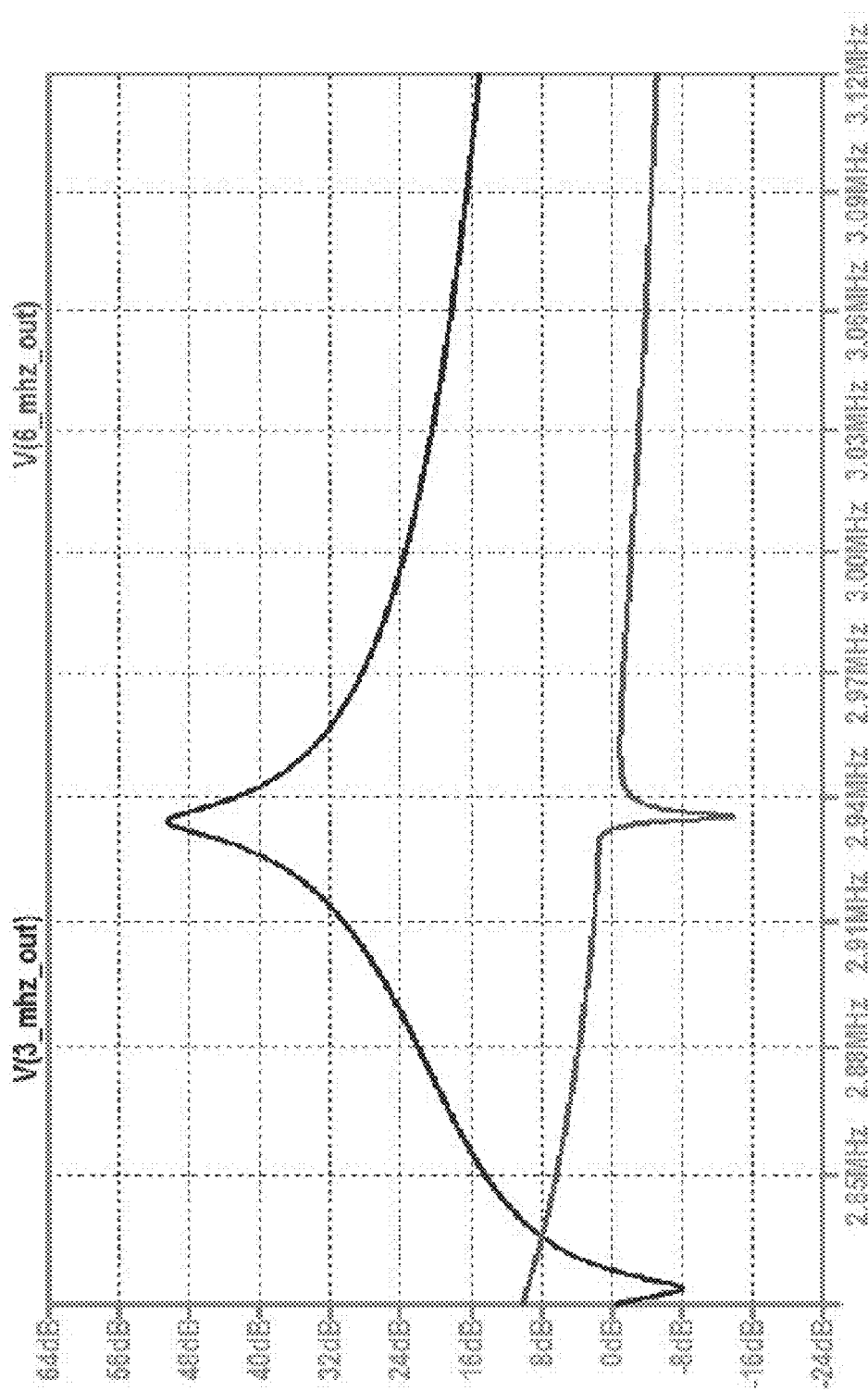
FIG. 15 shows gain of the 3 Mhz drive signal and the reduction of crosstalk on the 6 MHz side.

FIG. 15 shows the gain and crosstalk components when one of these peaks is chosen. The 3 MHz drive signal achieves upwards of 50 dB of gain on the appropriate side of the cell, while reducing crosstalk on the 6 MHz side of the cell to about −14 dB.

Figure 16:
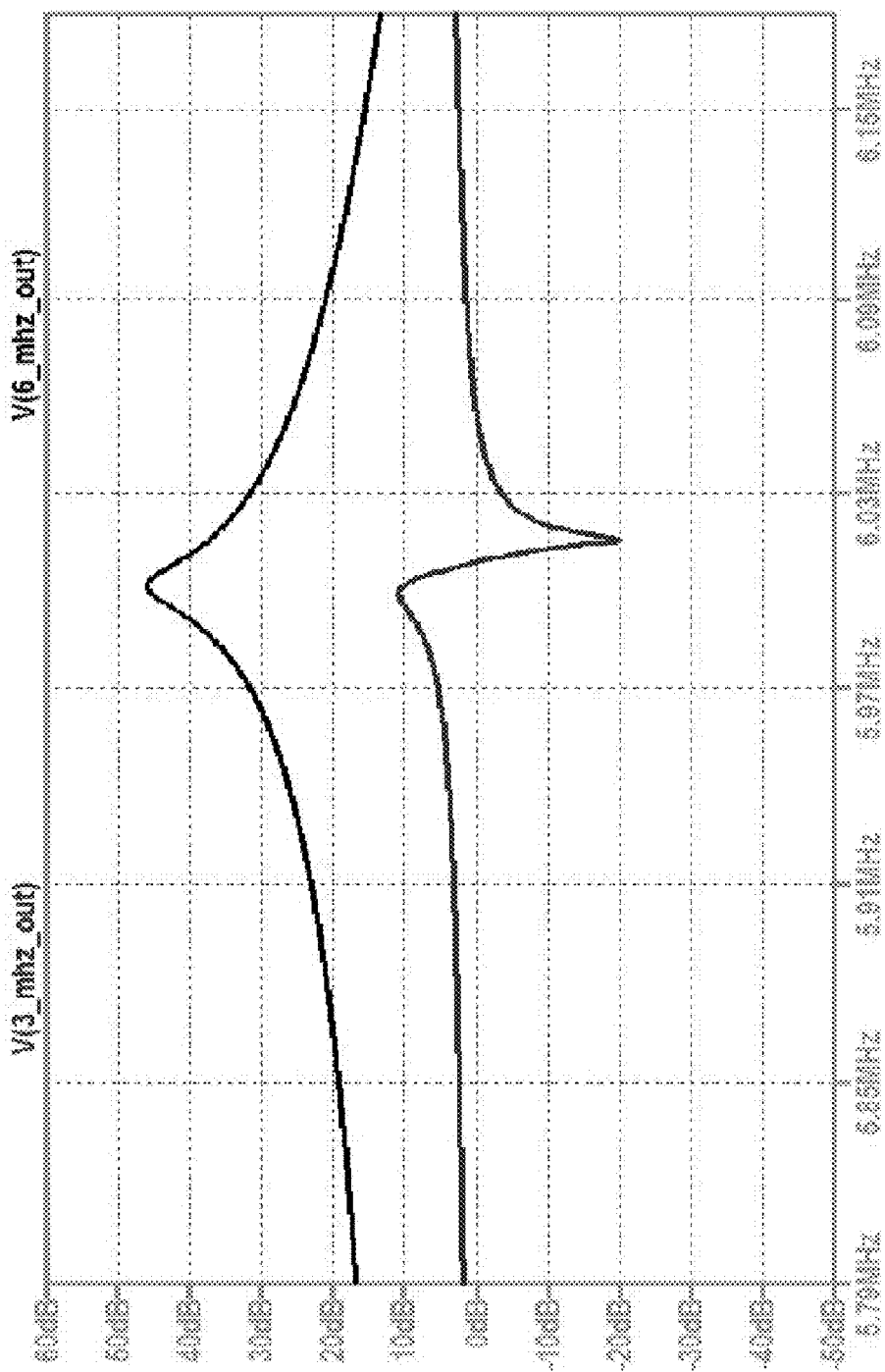
FIG. 16 shows gain of the 6 Mhz drive signal and the reduction of crosstalk on the 3 MHz side.

FIG. 16 shows a similar result at 6 MHz. The uppermost signal shows the gain of the 6 MHz signal on the appropriate side of the cell, while the crosstalk component (bottom signal) is substantially lower. Contrast FIGS. 15 and 16 to FIGS. 9 and 10 and the utility of this approach can be seen.

Figure 17:
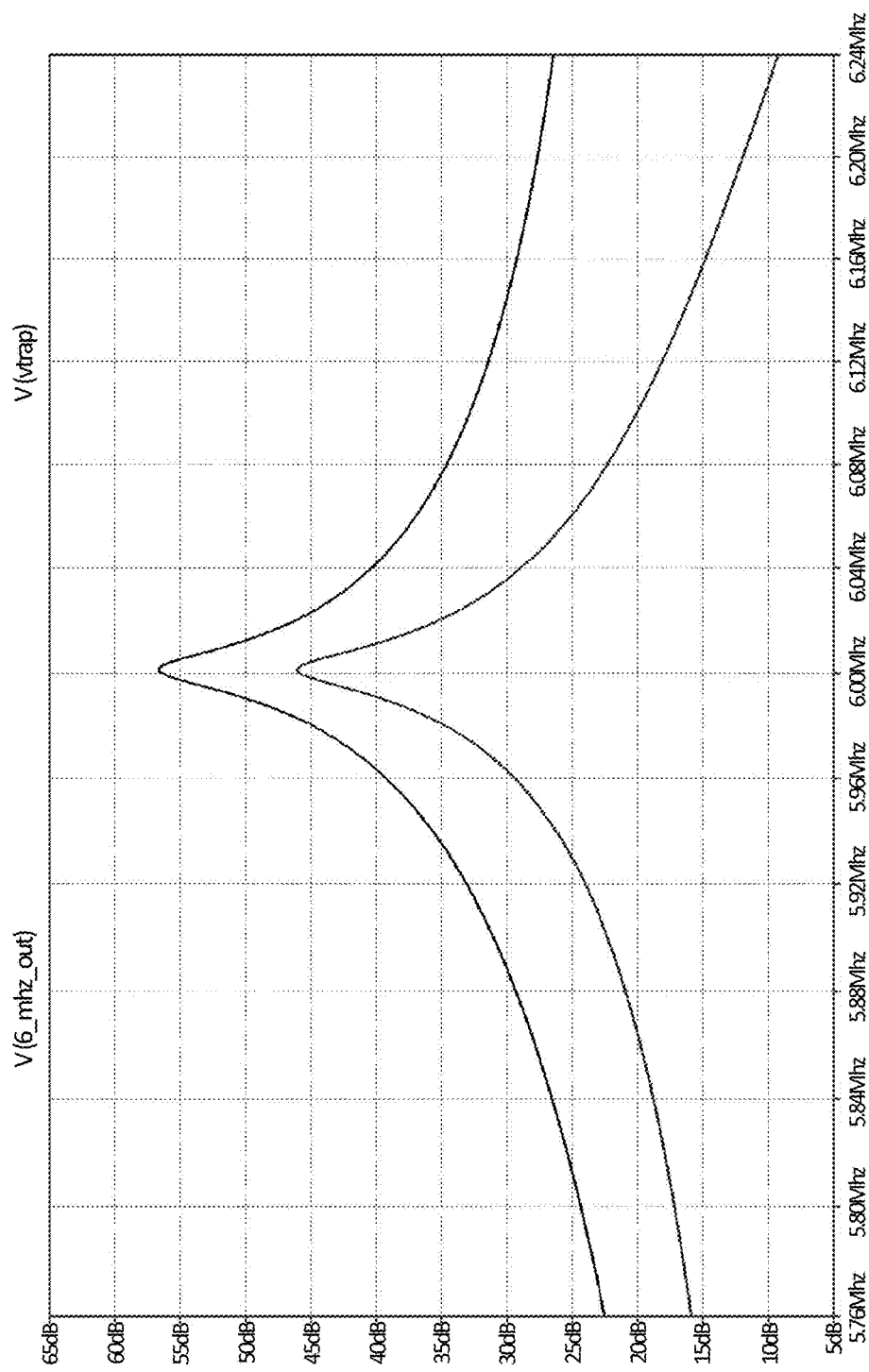
FIG. 17 shows a comparison of the voltage in the 3 MHz trap to the cell voltage.

FIG. 17 compares the voltage in the 3 MHz trap to the cell voltage. Here, the lowermost signal is the cell voltage on the appropriate side of the mobility cell. The uppermost cell is the voltage at a point inside the 3 MHz-side trap, between L4 and C2. The fact that the voltage within the notch filter is higher than the cell voltage indicates that this approach may have an efficiency loss. The overall efficiency can be improved by selecting coils for the trap filters with higher inductance. These trap coils lose power because the traps effectively short undesired signal components to ground on the appropriate side of mobility cell. While this may result in an efficiency loss, this can be acceptable given the obvious benefits to mitigating crosstalk by using these notch filters.

Compensation Circuit 2

Figure 18:
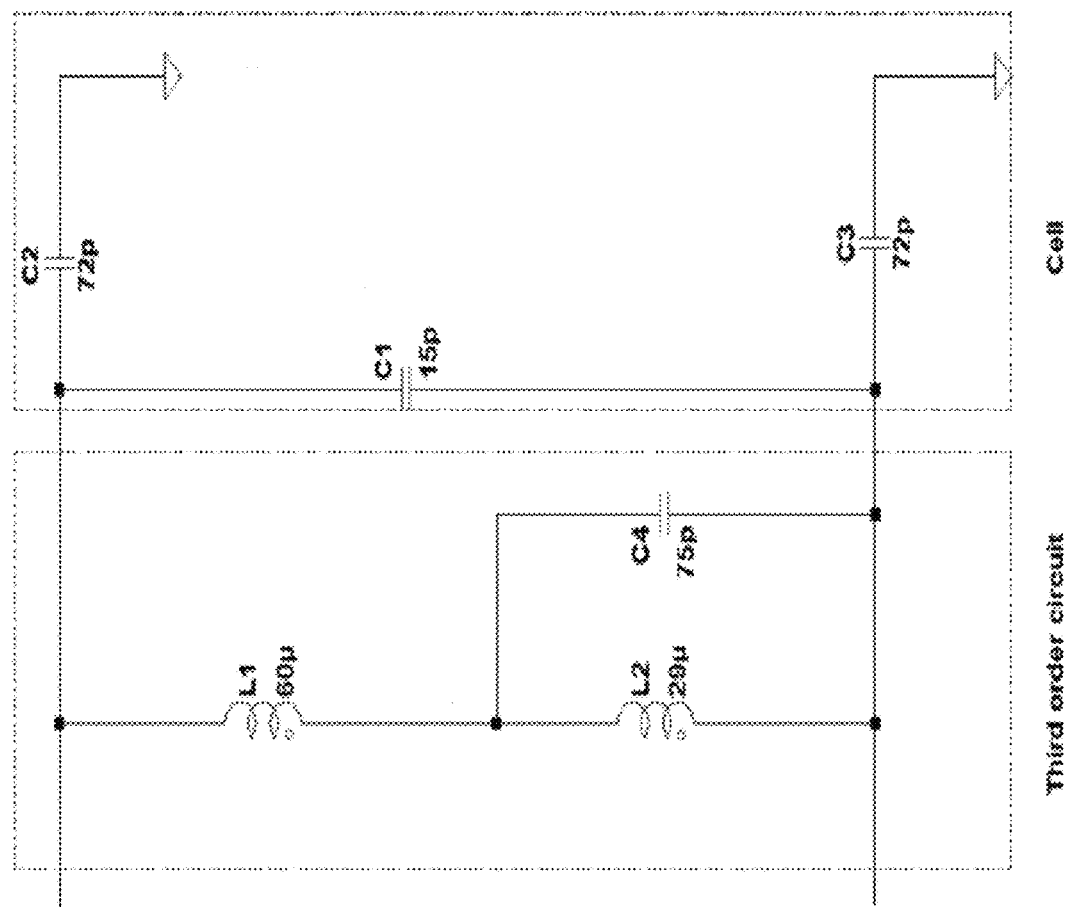
FIG. 18 shows another exemplary embodiment of a crosstalk compensation circuit that utilizes a third order circuit.

Another embodiment of a compensation circuit that may be used to compensate for crosstalk across the mobility cell is shown in FIG. 18. Here, voltage sources V1 and V2 are not shown. In FIG. 18, a third order circuit is placed in parallel to the mobility cell C1. The mobility cell shown is the existing shorter mobility cell in the prior art. In parallel with cell C1, the third order circuit becomes a fourth order circuit. The third order circuit can be thought of as adding negative capacitance to prevent crosstalk from occurring across cell C1.

The third order circuit creates a large impedance at each side of the cell for the frequencies to be rejected. This can greatly reduce or substantially eliminate crosstalk without shorting crosstalk signals to ground, which may result in increased efficiency. The values of components L1, L2, and C4 in the third order circuit are chosen so that, with C1, there is a high impedance at 3 and 6 MHz. The resulting fourth order circuit essentially appears as an open circuit between the two sides of cell C1, substantially eliminating crosstalk.

Effectively, two parallel resonances are created by the fourth order circuit. Inductors L1 and L2 will generally have the same ratio as the ratio of the two resonant frequencies, 3 and 6 MHz. The behavior of the resulting fourth order circuit and the selection of the appropriate components to create the appropriate resonances can be understood by analyzing a transfer function. The transfer function and the selection of components can be readily understood by a person of ordinary skill in the art in accordance with the present teachings.

Compensation Circuit 3

Figure 19:
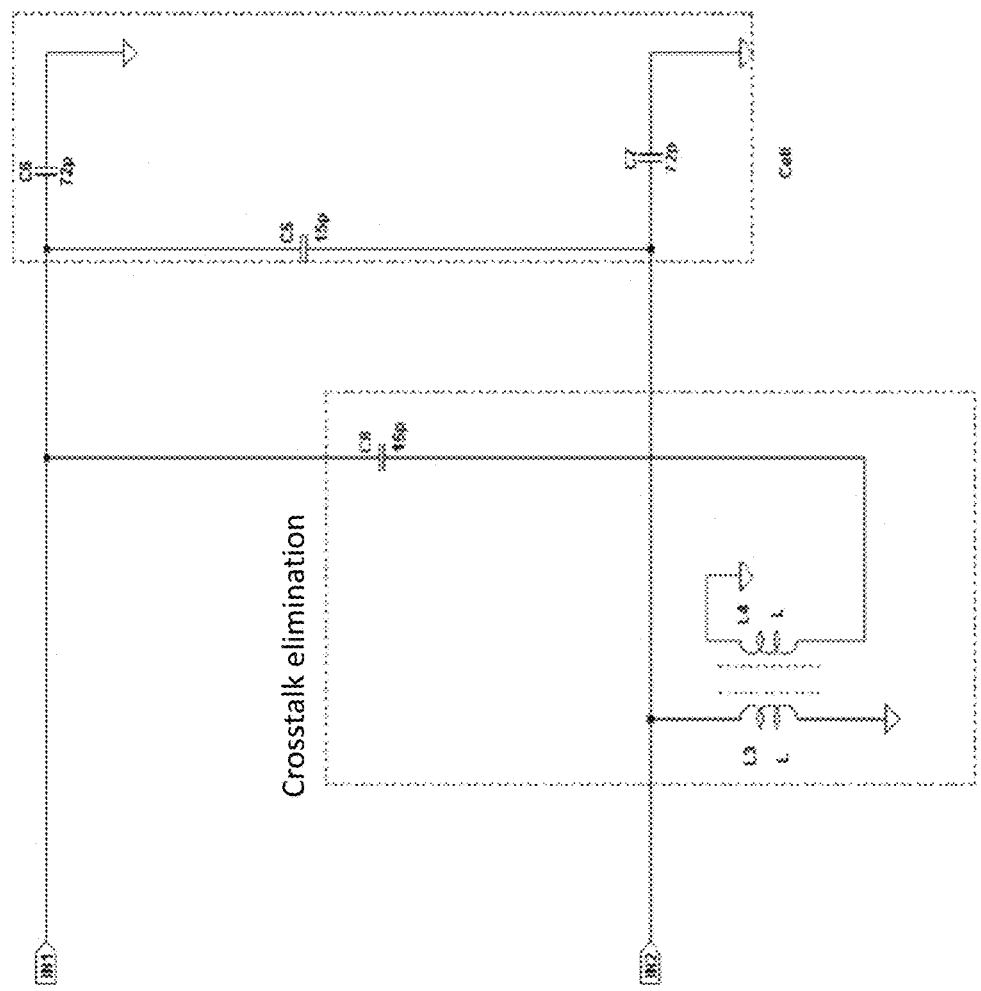
FIG. 19 shows another exemplary embodiment of a crosstalk compensation circuit that comprises a two winding transformers.

Another embodiment of a crosstalk compensation circuit is illustrated in FIG. 19. The compensation circuit comprises a two winding transformer and a capacitor that substantially matches the capacitance of the mobility cell. Like FIG. 18, the high voltage waveform generator components are not shown The compensation circuit in FIG. 19 magnetically couples components of the temporally periodic signals (e.g., sinusoidal signals) generated by the waveform generator. By adding capacitor C8 and selecting how the transformer is tapped, the resulting signals at each side of the cell picked up from this magnetic coupling are out of phase. The out of phase signals substantially cancel out the crosstalk signals that result from the gap in the mobility cell. Each coil of the transformer creates a path to ground. The windings are arranged to provide out of phase outputs. The transformer can include windings with a high number of turns to minimize the amount of current that will go to ground. As used herein, the term substantial should be understood to have its ordinary meaning or within about 5% of some related value, to the extent there is any confusion.

As discussed above, though a possible alternate solution to present teachings can be to dramatically increase the capacitive load of the wiring harness such that the same ratio of cell capacitive load/total capacitive load is maintained, it will be appreciated that the total capacitive load may need to increase by a factor of at least 2.5. The power requirements of the system would thus increase dramatically, likely requiring changes to coils, drivers, cooling system, and other components.

In summary, increased gas flow through the orifice of the mobility cell in high-flow DMS instruments requires a corresponding increase in size of the DMS cell, which increases the capacitance of the cell (and the total system). Use of an uncompensated DMS power supply may result in RF pick-up across the electrode gap, causing distortions of the separation field, thus providing poor separations, which directly affect data quality. The crosstalk compensation circuits disclosed herein in accordance with various aspects of the applicant's present teachings permit the use of higher capacitance DMS cells with existing waveform generators, and can potentially allow reducing the size of the waveform generator and associated wiring.

Those having ordinary skill in the art will appreciate that various changes can be made to the above embodiments without departing from the scope of the invention. In particular, the examples provided above relate to an asymmetric waveform generator designed to provide a separation waveform at 3 MHz. The frequency can be changed without departing from the scope of this disclosure. For instance, higher frequency generators generally provide improved ion transmission with DMS devices due to reduction of the amplitude of radial oscillations, particularly when used with devices that have very small gap heights. Additionally, the examples provided above were described in the context of a planar geometry DMS device. These approaches may also be applied to curved geometry devices and micro-machined devices without deviating from the scope of these teachings. Finally, the examples provided above related to the use of a 13 cm DMS cell. The gap height, width, and length of the DMS cell may be varied without deviating from the scope of these teachings. The compensation approaches described above in accordance with various aspects of the applicant's teachings may be used with any cell geometry. While the exemplary embodiments described above include a DMS cell sealed to an inlet orifice of a mass spectrometer, the applicant's teachings may also be applied to mass spectrometer systems which have a capillary or heated capillary inlet. The applicant's teachings may also be applied to systems where the DMS or FAIMS cell is not sealed to a mass spectrometer.

It will be appreciated that for clarity, the above discussion explicates various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The above detailed description of embodiments is not to be regarded as limiting the scope of the applicant's teachings in any manner.

The skilled person in the art will understand that the drawings, described below, are for illustration purposes only. The drawings are not intended to limit the scope of the applicant's teachings in any way. For convenience, reference numerals may also be repeated (with or without an offset) throughout the figures to indicate analogous components or features.

What is claimed is:

1. An ion mobility system comprising:
    an ion mobility cell comprising at least a first and a second electrode that are substantially uniformly spaced, the ion mobility cell having a cell capacitance;
    a first high-voltage waveform generator configured to produce a first temporally periodic signal at a first frequency and at a first amplitude, the first waveform generator electrically coupled to the first electrode;
    a second high-voltage waveform generator configured to produce a second temporally periodic signal at a second frequency and at a second amplitude, the second waveform generator electrically coupled to the second electrode, the second frequency being a harmonic of the first frequency;
    a crosstalk compensation circuit configured to reduce crosstalk between the first and second electrodes such that application of the first and second temporally periodic signals results in an electric field in the ion mobility cell that is asymmetric and has a time-averaged value substantially equal to zero,
    and wherein the crosstalk compensation circuit comprises:
    a first filter electrically coupled to the first electrode and configured to substantially filter signal components at the second frequency;
    and a second filter electrically coupled to the second electrode and configured to substantially filter signal components at the first frequency;
    wherein the first and second filters are notch filters.

2. The ion mobility system of claim 1, further comprising a mass spectrometer coupled to an output of the ion mobility cell; and optionally
    wherein the ion mobility cell comprises one of a DMS and a FAIMS.

3. A high-field asymmetric-waveform apparatus comprising:

a first high-voltage waveform generator configured to produce a first temporally periodic signal at a first frequency and at a first amplitude, the first waveform generator configured to electrically couple to a first electrode of an ion mobility cell;

a second high-voltage waveform generator configured to produce a second temporally periodic signal at a second frequency and at a second amplitude, the second waveform generator configured to electrically couple to a second electrode of the ion mobility cell, the second frequency being a harmonic of the first frequency; and a crosstalk compensation circuit configured to reduce crosstalk between the first and second electrodes such that electrical signals at the first and second electrodes are configured to create an electric field in the ion mobility cell that is asymmetric and has a time-averaged value substantially equal to zero, wherein the crosstalk compensation circuit comprises:

a first filter electrically coupled to the first electrode and configured to substantially filter signal components at the second frequency;

and a second filter electrically coupled to the second electrode and configured to substantially filter signal components at the first frequency;

wherein the first and second filters are notch filters.

4. The high-field asymmetric wave apparatus of claim 3, wherein the ion mobility cell comprises one of a DMS and FAIMS; and optionally further comprising a mass spectrometer coupled to an output of the ion mobility cell.

5. A method for reducing crosstalk in an ion mobility spectrometer comprising:

providing an ion mobility cell comprising at least a first and a second electrode that are substantially uniformly spaced, the ion mobility cell having a cell capacitance;

providing a first temporally periodic signal at a first frequency and at a first amplitude with a first waveform generator, the first waveform generator electrically coupled to a first electrode of an ion mobility cell;

providing a second temporally periodic signal at a second frequency and at a second amplitude with a second waveform generator, the second waveform generator electrically coupled to a second electrode of the ion mobility cell, the second frequency being a harmonic of the first frequency;

utilizing a crosstalk compensation circuit to reduce crosstalk between the first and second electrodes such that application of the first and second temporally periodic signals results in an electric field in the ion mobility cell that is asymmetric and has a time-averaged value substantially equal to zero, wherein the crosstalk compensation circuit comprises:

a first filter electrically coupled to the first electrode and configured to substantially filter signal components at the second frequency;

and a second filter electrically coupled to the second electrode and configured to substantially filter signal components at the first frequency;

wherein the first and second filters are notch filters.

6. The method of claim 5, wherein the first and second electrodes of the ion mobility cell are substantially uniformly spaced, the ion mobility cell exhibiting a cell capacitance.

7. The method of claim 5 further comprising, providing a mass spectrometer coupled to an output of the ion mobility cell.

* * * * *